United States Patent
Jönsson

(10) Patent No.: US 9,814,464 B2
(45) Date of Patent: Nov. 14, 2017

(54) POST OPERATIVE WOUND SUPPORT DEVICE

(75) Inventor: Anders Jönsson, Bromma (SE)

(73) Assignee: AEEG AB, Helsingborg (SE)

( * ) Notice: Subject to any disclaimer, the term of this patent is extended or adjusted under 35 U.S.C. 154(b) by 721 days.

(21) Appl. No.: 13/575,287

(22) PCT Filed: Jan. 27, 2011

(86) PCT No.: PCT/EP2011/051178
§ 371 (c)(1),
(2), (4) Date: Aug. 16, 2012

(87) PCT Pub. No.: WO2011/092268
PCT Pub. Date: Aug. 4, 2011

(65) Prior Publication Data
US 2012/0316491 A1 Dec. 13, 2012

(30) Foreign Application Priority Data
Jan. 27, 2010 (EP) .................................... 10151829

(51) Int. Cl.
*A61M 25/00* (2006.01)
*A61B 17/12* (2006.01)
(Continued)

(52) U.S. Cl.
CPC .... *A61B 17/12022* (2013.01); *A61B 17/0057* (2013.01); *A61B 17/12099* (2013.01);
(Continued)

(58) Field of Classification Search
CPC . A61M 27/00; A61M 1/0084; A61B 17/0057; A61B 17/12136
See application file for complete search history.

(56) References Cited

U.S. PATENT DOCUMENTS

| | | | |
|---|---|---|---|
| 3,908,664 A | 9/1975 | Loseff | |
| 5,213,576 A | 5/1993 | Abiuso et al. | |

(Continued)

FOREIGN PATENT DOCUMENTS

| | | |
|---|---|---|
| DE | 203 20 631 U1 | 1/2005 |
| EP | 0 668 086 A1 | 8/1995 |

(Continued)

OTHER PUBLICATIONS

WIPO, European International Preliminary Examining Authority, International Preliminary Report on Patentability dated May 11, 2012 in International Patent Application No. PCT/EP2011/051178, 6 pages.

(Continued)

*Primary Examiner* — Emily Schmidt
(74) *Attorney, Agent, or Firm* — Inskeep IP Group, Inc.

(57) ABSTRACT

A wound drainage and hemostasis promoting medical device (1) are disclosed. A balloon (15) is temporary inflated and arranged outside a sheath (10), in contact with tissue surrounding a wound cavity for hemostasis promotion. The drainage device comprises a fluid communication channel for wound exudate from wound. The balloon is deflated and retracted into said sheath for removal from said wound cavity. Thus the medical device is percutaneously retractable from said confined wound.

17 Claims, 11 Drawing Sheets

(51) Int. Cl.
  *A61B 17/00* (2006.01)
  *A61M 1/00* (2006.01)
  *A61M 37/00* (2006.01)
  *A61M 25/10* (2013.01)
(52) U.S. Cl.
  CPC ....... *A61B 17/12136* (2013.01); *A61M 1/008* (2013.01); *A61M 1/0096* (2014.02); *A61B 2017/00676* (2013.01); *A61B 2017/00893* (2013.01); *A61B 2017/12004* (2013.01); *A61M 37/0092* (2013.01); *A61M 2025/0002* (2013.01); *A61M 2025/006* (2013.01); *A61M 2025/0059* (2013.01); *A61M 2025/1015* (2013.01); *A61M 2025/1075* (2013.01); *A61M 2025/1081* (2013.01); *A61M 2025/1084* (2013.01); *A61M 2025/1088* (2013.01)

(56) References Cited

U.S. PATENT DOCUMENTS

| | | | |
|---|---|---|---|
| 5,545,176 | A | 8/1996 | Murtfeldt |
| 6,364,856 | B1 | 4/2002 | Ding et al. |
| 2002/0068180 | A1 | 6/2002 | Yang et al. |
| 2002/0094985 | A1* | 7/2002 | Herrmann et al. ........... 514/245 |
| 2002/0156495 | A1 | 10/2002 | Brenneman et al. |
| 2005/0015047 | A1 | 1/2005 | Shah |
| 2005/0154416 | A1* | 7/2005 | Herweck ............... A61L 29/041 606/194 |
| 2007/0243224 | A1* | 10/2007 | Ludwig ................ A61K 31/198 424/423 |
| 2008/0119785 | A1 | 5/2008 | Ramsey et al. |
| 2008/0215031 | A1* | 9/2008 | Belfort et al. ................ 604/500 |
| 2008/0249464 | A1 | 10/2008 | Spencer et al. |
| 2010/0152683 | A1* | 6/2010 | Lindgren ............... A61K 9/703 604/306 |
| 2011/0082414 | A1* | 4/2011 | Wallace ............ A61M 37/0092 604/22 |
| 2012/0323217 | A1* | 12/2012 | Abrahams ..................... 604/506 |

FOREIGN PATENT DOCUMENTS

| | | |
|---|---|---|
| LU | 90 613 A1 | 7/2000 |
| WO | WO 03/024318 A1 | 3/2003 |
| WO | WO 2005/092204 A2 | 10/2005 |
| WO | WO 2007/081448 A2 | 7/2007 |
| WO | WO 2008/100433 A2 | 8/2008 |
| WO | WO 2009/120761 A1 | 10/2009 |
| WO | WO 2009/153973 A1 | 12/2009 |

OTHER PUBLICATIONS

WIPO, European International Search Authority, International Search Report dated Apr. 29, 2011 in International Patent Application No. PCT/EP2011/051178, 8 pages.

\* cited by examiner

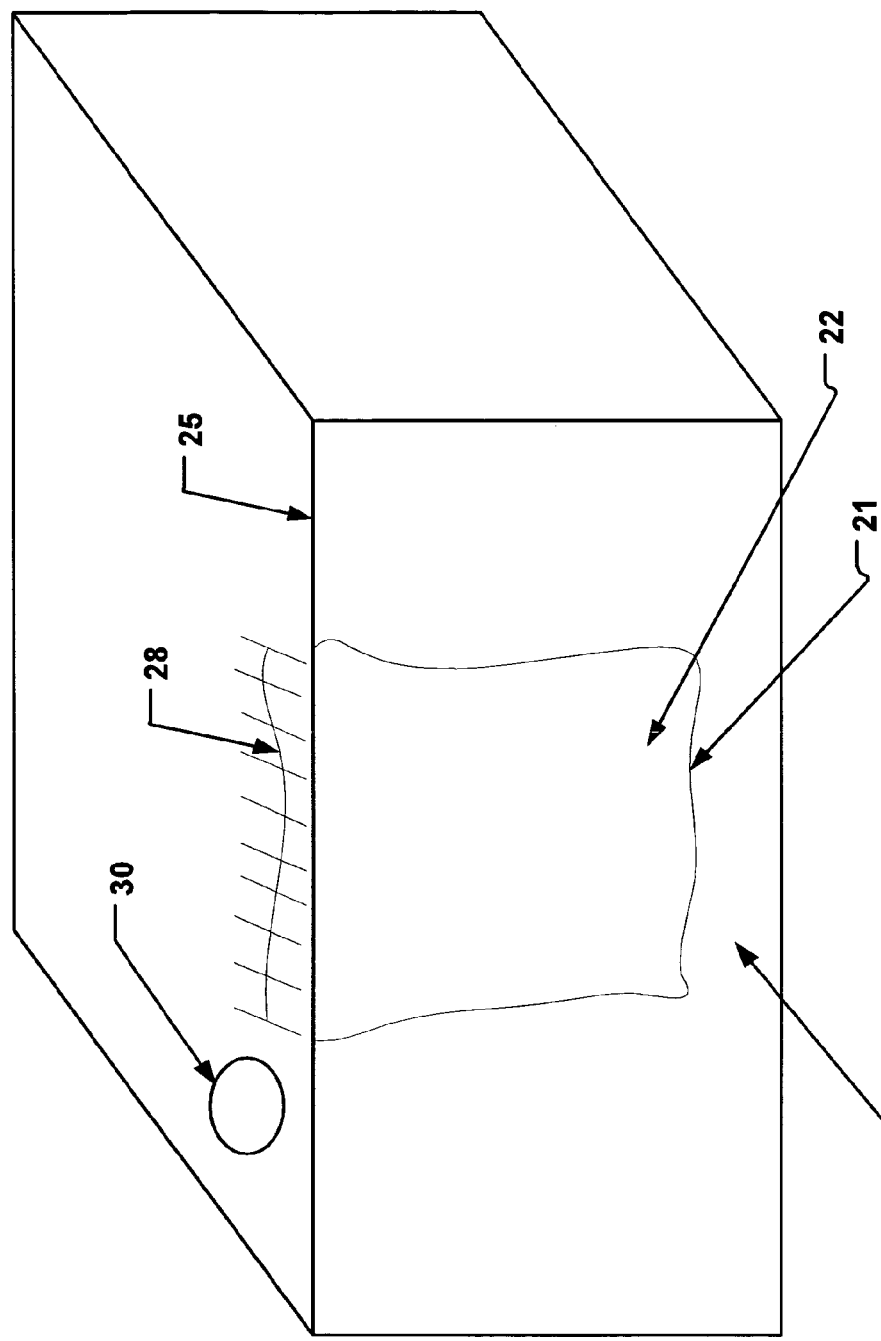

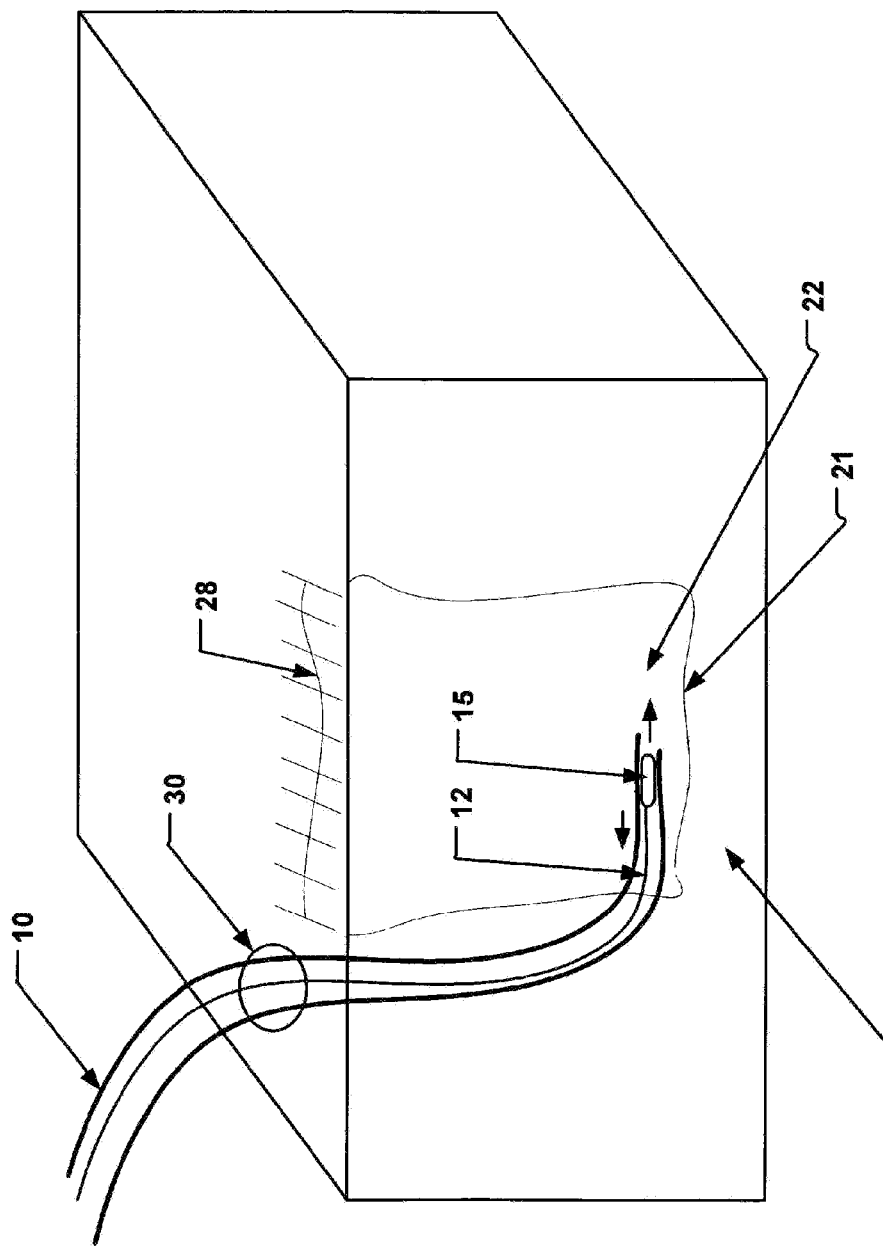

POST OPERATIVE WOUND SUPPORT DEVICE

RELATED APPLICATIONS

The present application is the U.S. National Phase of International Patent Application No. PCT/EP2011/051178, International Filing Date 27 Jan. 2011, entitled Post Operative Wound Support Device, which claims benefit of European Patent Application No. 10151829.8, filed 27 Jan. 2010, entitled Post Operative Wound Support Device And Method, both of which are incorporated herein by reference in their entireties.

FIELD OF THE INVENTION

This invention pertains in general to the field of medical devices. More particularly the invention relates post operative wound support devices and procedures, and more particularly to such devices and procedures related to bleeding control and wound exudate handling of confined wounds, including draining of the exudate and promoting hemostasis in subcutaneous tissue surrounding a wound cavity of the confined wound.

BACKGROUND OF THE INVENTION

Hemostasis is a complex process which causes a bleeding process of a wound to stop. It refers to a multiple step process of repairing damaged blood vessels, including vasoconstriction, bleeding blockage by platelet aggregation, and a series of enzymatic reactions that ends in the formation of a fibrin protein fiber mesh that stabilizes the platelet plug to a clot.

In international patent application WO0222059A1, it is disclosed that bleeding wounds may be treated by applying pressure directly in the bleeding wound by applying a back pressure in a confined space around and in the wound. Substances or articles are inserted into the wound, and the wound may be enclosed with that substance or article encountered in the wound. The substance is for instance a hemostatic substance that is swelling on contact with blood and generates a pressure to stop or reduce the bleeding without the detrimental effects of a tourniquet. A wound dressing using this technology is provided that is either removable for a definitive treatment or biodegradable if not removed. When bleeding stops after insertion of such a device into a bleeding wound, the expanded device may be permitted to remain in the wound or may be removed. It is stated in WO0222059A1 that a decision whether to remove the expanded device or not is taken based on the need for access to the internal wound area for surgery, etc. Preferably the device is left in the patient unless the device needs to be removed from the wound for access to the internal wound area.

WO0222059A1 deals with devices for treatment of acute wounds, such as combat wounds before a surgical intervention.

An application for treatment of post-operative surgical confined wounds, that are cutaneously closed, is not foreseen in WO0222059A1. The devices and methods disclosed in WO0222059A1 are not suited for this purpose as there is for instance a desire that post-operative surgical confined wounds are not opened again unnecessarily.

In application U.S. 2008/0119785 an inflatable balloon for "wound track navigation and hemorrhage control" is disclosed. The balloon is to be inserted into a wound track to provide pressure to the surrounding wound tissue. No wound healing promoting is disclosed likewise modalities for the inhibition of tissue adhesion. The balloon may thus adhere to the wound and injure the patient upon removal of the device from the wound.

In application DE20320631U1, a medical device to be used in a healing process comprising flexible inflatable tube is disclosed. The balloon is also placed on the outside of the catheter, which may result in complications when removing the device from enclosed wounds. Neither wound treatment nor stopping of bleeding is disclosed in this document.

In application LU 90613A1 an intra- and peri-articular catheter is disclosed. A balloon is employed to apply pressure to artery walls to reduce intra- and peri-articular hemorrhages. The catheter can be used to drain wound exudates and surrounding the front end on the outside is the inflatable balloon used for applying pressure to the tissue. However due to the balloon being on the outside of the catheter removal from an enclosed wound would required reopening the wound, thus increasing the chances for infection.

In application WO 2009/120761 A1, an instrument for controlling bleeding at surgical sites is disclosed. An inflatable balloon is inflated to apply pressure to a wound. No fluid drainage is provided for neither is the use of further wound healing modalities. This is a device for very acute treatment. The balloon is spherical or toroidal and does not efficiently adapt to wound tissue topography. A wound healing process in a confined wound is not supported by this device.

In application U.S. 2002/0156495 A1, an apparatus for percutaneous sealing of blood vessel punctures is described. An inflatable balloon is used to seal primarily injured blood vessels and as such no wound drainage is provided for likewise initial wound healing.

In application U.S. 2005/0154416 A1, a therapeutic agent delivery system is disclosed. This device is designed to facilitate fluid release to the surrounding bodily tissue. The device is for very short term use in percutaneous transluminal angioplasty (PTA) applications and not suitable for stopping bleeding in confined wounds. A hydrophobic, biocompatible member with low friction is disclosed. No wound drainage devices or wound treatment are provided.

In application U.S. 2007/0243224 A1 describes methods and compositions for treating lesioned site of body vessels. Primarily nitric oxide (NO) is used to induce apoptosis of macrophages cells at lesioned site of a body vessel. A balloon is not described. A applying pressure to a wound similarly is not disclosed. NO is delivered to the vessel in gaseous form, as an aqueous solution, or from a stent. Moreover, NO in this context is used to reduce atherosclerotic plaque build up in contrast to NO being used to counter potential infections as with its use in the wound healing scenario.

In application U.S. 2008/0249464, a catheter having internal mechanisms to encourage balloon re-folding are disclosed. The device is to be used primarily for short-term angioplasty treatment procedures therefore the balloon used for these procedures is required to be rewrapped about the catheter shaft. The balloon therefore is on the outside of the device and is not designed to enter a sheath like structure. Furthermore no wound healing mechanisms are provided. There is no disclosure of a stent inside a balloon to support patency of the balloon.

In application WO 2009/153973 a rectal catheter and penetration enhancing system for enema drug delivery is provided. A vibrating inflatable balloon is employed in the intestines to enhance intestinal drug uptake. Neither wound healing is described nor wound drainage.

Hence, improved or alternative medical devices and procedures for treatment of post-operative surgical confined wounds would be advantageous, in particular allowing for increased flexibility, cost-effectiveness, and/or patient safety for said treatment would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a medical device and a method according to the appended patent claims.

A wound drainage and hemostasis promoting medical device and procedure are disclosed. A balloon is temporary inflated and arranged outside a sheath, in contact with tissue surrounding a wound cavity for hemostasis promotion. The drainage portion of the device comprises a fluid communication channel for wound exudate from a wound. The balloon is deflated and retracted into the sheath for removal from the wound cavity. Thus the medical device is percutaneously retractable from the confined wound.

According to one aspect of the invention a device is disclosed, whereby the device has a hemostasis promoting medical device adapted to promote hemostasis in subcutaneous tissue surrounding a wound cavity of a post surgical wound in the tissue, wherein the wound is a confined wound that is cutaneously closed. The device has an elongate sheath having a proximal end in use arranged outside the wound cavity and a distal end in use percutaneously delivered into and arranged in the wound cavity. Further, the device has a hollow inflation and deflation tubular member arranged along the elongate sheath, and an inflatable and deflatable balloon in fluid communication with the tubular member, the balloon being arranged at the distal end longitudinally moveable relative the sheath. The balloon is temporary inflated and arranged outside the sheath, at least partly in contact with the tissue for the hemostasis promotion, and deflated and arranged proximal to the distal end inside the sheath for delivery to the wound cavity prior to being temporary inflated in the wound cavity, and for removal from the wound cavity when the deflated balloon is retracted into the sheath or the sheath is pushed over the deflated balloon, for removal of the device from the wound cavity. In such a manner the hemostasis promoting medical device is percutaneously retractable from the confined wound.

In some embodiments the balloon and/or the sheath have an outer surface that is at least partly non-absorbent for liquid and/or non-adhesive to the tissue. This provides for easy removal of the device. A non-absorbant surface or membrane of the balloon and/or the sheath prevents that wound exudate is retained therein. This allows for easier retraction of the balloon into the device as it has not gained in mass. Further, as blood coagulates in the wound during hemostasis, the blood clot is kept apart from the surface. Thus, the balloon and/or the sheath of the device do not stick to the blood clot upon wound healing. Removal of the device after initial wound healing is facilitated. The balloon is thus easily retracted without tearing open the wound again. A similar reasoning applies to a non-adhesive surface or membrane of the balloon and/or the sheath.

In some embodiments the surface is hydrophobic such that for instance clotted blood in the wound cavity does not stick to the balloon and/or sheath. The non adherence of the balloon to the surrounding tissue is provided by the hydrophobic surface thereof. This is in particular advantageous for the long-term use of the medical device. Long-term use means several hours or days. Examples are given below. This is a long-term in contrast to short-term, such as in percutaneous transluminal angioplasty (PTA) procedures and devices which typically are used for some minutes and then withdrawn from the patient. Blood clotting does not occur at such devices to a rate that would make the balloon stick to the vessel. Hence, devices of the embodiments of the invention provide a balance of clot formation in the wound tissue and surrounding vasculature as opposed to formation on the balloon. Pro-coagulation is promoted. This is the early phase of wound healing, important for controlling a bleeding situation. The device can be removed from the wound without causing a new bleeding situation, as e.g. a ripping out from a partly healed wound is prevented. Blood products from blood banks are saved. Blood transfusions are minimized or avoided. In this manner, patient care is provided more cost-effective. Moreover, pain management is effectively provided.

Non-adhesive, non-absorbent and hydrophobic properties may in some embodiments advantageously be provided in arbitrary combinations to further synergistically enhance these advantages.

In some embodiments the balloon has a foamy outside structure, such as a cell structure of foam rubber. This allows for a careful, soft and smooth apposition to the tissue surrounding the wound cavity, avoiding too high mechanical pressures on the tissue. In particular when being hydrophobic, the foamy outside does not stick to the surrounding wound tissue when healing (clotting).

In some embodiments the sheath is flexible. In this manner the distal portion of the device is for instance easily positionable in the wound before it is closed, as the sheath is easily bent and allowable curvatures of the sheath allow for flexible use, including insertion in a subcutaneous wound cavity in a direction parallel to the skin in tissue around the wound cavity.

In embodiments the balloon has a membrane that is fluid impermeable. Thus exudate is preventing from entering the balloon. Further, an inflation fluid is prevented from entering the wound cavity through such a membrane of the balloon. This provides for instance for a reduced risk of infections.

In some embodiments the balloon has a membrane that is non-swelling. This provides for a precisely controllable mechanical pressure applied by the balloon. Further, retraction into the sheath is facilitated as the volume of the deflated balloon is not increased after application and thus the inner diameter of the sheath is sufficient for retracting the balloon.

In some embodiments the balloon has a surface that comprises a pharmaceutical substance, e.g. as coating, e.g. of antibiotics, coagulation promoting agents, platelet adherence reducer. This allows for a controllable and improved healing process of the wound.

In some embodiments the balloon is permeable for nitric oxide (NO), and when inflated filled with a liquid releasing the NO. NO has a number of advantageous properties, such as anti-pathogenic, anti-viral, anti-bacterial properties that enhance wound healing. However, NO has a very short half-life and was hitherto difficult to provide to wounds in a practical manner. A level of NO may thus be maintained the relatively long periods of time as required by the present device. NO provides an alternative to conventional therapies, such as antibiotics.

In some embodiments the balloon is made of polytetrafluoroethylene (PTFE) or hydrophobic microporous polytetrafluoroethylene (PTFE). PTFE allows for easy removal of the device.

In some embodiments the balloon has arranged therein a bistable support stent that has a first collapsed configuration when the balloon is deflated and a second expanded configuration when the balloon is inflated for supporting a patency of the balloon in the wound cavity. Being bistable, the stent is collapsible to its initial shape when deflating the balloon. This allows for easy retrieval of the device. As the stent extends substantially over the entire length of the balloon, it advantageously provides for patency of the balloon. Internal pressure of the balloon may be kept low, providing for a "soft", tissue friendly inflation while providing reliable stopping of bleeding.

In some embodiments the device has a pressure sensor for regulating an inner pressure of the balloon when inflated in order to provide a desired size of the balloon in such a manner that a desired pressure is applied to the tissue. Thus, too undesired pressure are avoided. Too high pressure is avoided which may cause mechanical harm to surrounding tissue. Too low pressure is avoided, where tissue apposition is not reliably provided. A loss of inflation pressure during the application of the device may be detected and compensated by informing clinical personal or initiating auto inflation in a feedback loop.

In some embodiments the device has a pressure sensor for detection of a dislocation of the balloon when inflated for an alarm when a threshold pressure is crossed. Some types of dislocation may be detected upon crossing the threshold towards higher pressures than initially inflated. Some types of dislocation may be detected upon crossing the threshold towards lower pressures than initially inflated.

In some embodiments the device further comprises an ultrasonic sound generator adapted to provide ultrasonic therapeutic healing of the wound when the balloon is inflated with a liquid, wherein ultrasonic sound generator is coupled to the liquid and such that ultrasonic sound waves propagate through the liquid and the balloon to the tissue for the ultrasonic therapeutic healing. Alternatively, or in addition, the balloon or the distal end region of the sheath may be equipped with ultrasonic sound transducers, such as piezo crystals to provide the ultrasonic therapeutic healing at the wound site.

According to a further aspect of the invention, a combination of the hemostasis promoting medical device of the first aspect of the invention, and a medical drainage device is provided. The drainage device comprises a fluid communication channel for wound exudate from the wound, the channel having a distal end adapted to be arranged in the wound cavity.

The combination may be provided in form of a kit. Alternatively, the combination is provided by a single device in which the hemostasis promoting medical and the drainage device are monolithically integrated.

In some embodiments the fluid communication channel is integrally formed with the sheath, providing a medical drainage device with at least temporary hemostasis promoting properties.

According to another aspect of the invention, a method is provided, in form of a medical procedure of draining exudate from a wound cavity of a post surgical confined wound and promoting hemostasis for therapeutic treatment of the wound. The procedure comprises providing a medical drainage device having a fluid communication channel, and percutaneously arranging a distal end of the fluid communication channel in the wound cavity of the post surgical confined wound and a proximal end of the fluid communication channel outside of the wound cavity, and thus draining wound exudate from the distal end to the proximal end of the fluid communication channel; providing a hemostasis promoting medical device having an elongate sheath, an inflatable and deflatable balloon longitudinally moveable relative the sheath, and a hollow inflation and deflation tubular member along the elongate sheath in fluid communication with the balloon, and percutaneously arranging a proximal end of the elongate sheath outside the wound cavity and a distal end of the elongate sheath in the wound cavity with the balloon deflated in the sheath, discharging the balloon out of the distal end of the sheath in the wound cavity thereof, inflating the balloon to a desired pressure through the tubular member to be at least partly in apposition with tissue surrounding the wound cavity for the hemostasis promotion during a hemostasis promoting time, deflating the balloon, reloading the deflated balloon into the distal end of the sheath, and retracting the distal end of the sheath out of the wound cavity.

In this manner, uncontrolled bleedings are brought advantageously under control.

In embodiments the deflated balloon is reloaded into the sheath by moving the sheath longitudinally relative the balloon, including retracting the hollow tubular member and thus the balloon into the sheath, or pushing the sheath over the deflated balloon.

In some embodiments the hemostasis promoting time is between six and up to twenty-four hours, preferably between eight to twelve hours before deflating the balloon and withdrawing the balloon and/or sheath.

In some embodiments the procedure is a non-acute, planned procedure initiated during termination of a surgical intervention.

In some embodiments the surgical intervention is a thorax surgical intervention and the draining provides preventing of a tamponage by the wound cavity. A tamponage is an accumulation of liquid from bleeding in the wound that obstructs the cardiac work and needs immediate action in order to prevent cardiac damage.

In some embodiments a gas pressure lower than a gas pressure in the wound cavity is applied to the distal end of the fluid communication channel in the wound cavity for promoting the drainage. Wound exudate is removed from the wound cavity by suction, while at the same time a positive mechanical pressure is provided on at least a part of the tissue surrounding the wound cavity.

In some embodiments the inflated balloon provides a positive mechanical pressure at the apposition for the hemostasis promotion, and wherein the balloon is flexible to make contact with the tissue substantially independent of a topography of the tissue surrounding the wound cavity. The balloon thus adapts to any wound shape and maximizes the hemostasis promoting effect. In more detail, in some embodiments the balloon is resiliently stretchable by inflation to provide the flexible tissue topography adaptation.

In embodiments the confined wound thus needs not to be opened again during healing. This is a huge advantage as re-opening a wound has a large number of drawbacks, including risk of infection, tissue damage, interruption of healing, etc.

Further embodiments of the invention are defined in the dependent claims, wherein features for the second and subsequent aspects of the invention are as for the first aspect mutatis mutandis.

Some embodiments of the invention provide for reduced necessary blood to be transferred to a patient.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 4A to 4F are schematic views of a confined wound site where a hemostasis promoting medical device is applied;

DESCRIPTION OF EMBODIMENTS

Figure 1:
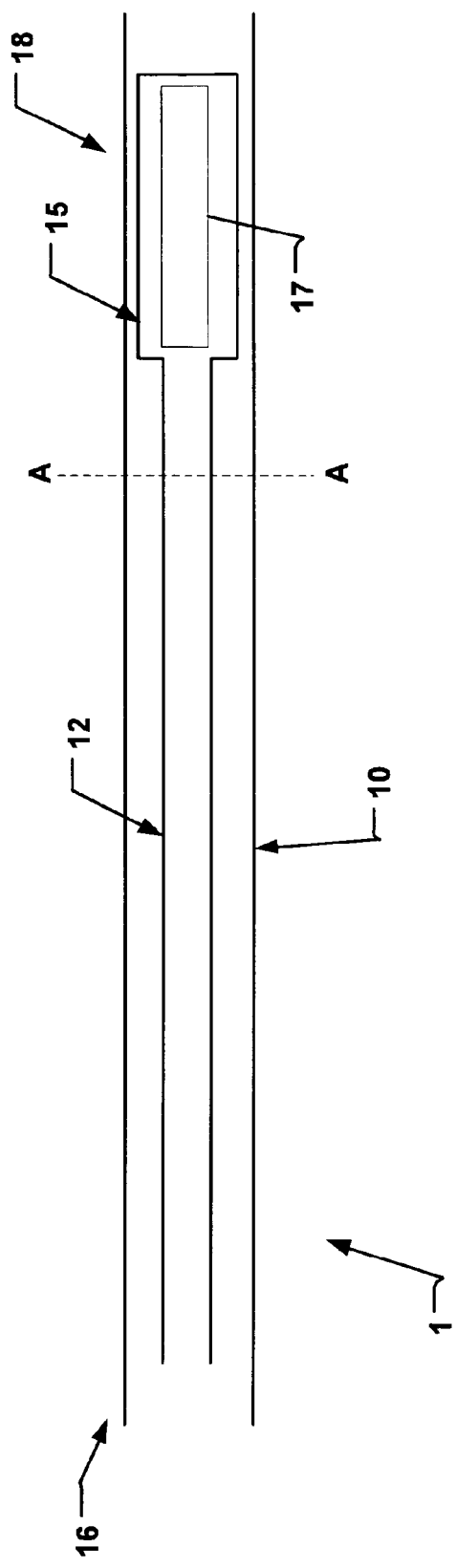
FIG. 1 is a longitudinal cross-sectional view of a hemostasis promoting medical device.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to an abdominal confined wound. However, it will be appreciated that the invention is not limited to this application but may be applied to many other confined wounds, e.g. in the limbs.

In embodiments a surgical wound bleeding reducer device and system comprising an inflatable balloon to be inserted into a surgical wound cavity during a healing phase thereof are provided. The balloon is inserted via a sheath, released in the cavity and inflated to a desired size. The balloon applies a positive mechanical pressure onto the surrounding wound tissue, thus minimizing bleeding and improving healing of the wound. Upon retraction, the balloon is deflated and retracted through the sheath out of the wound. This device is intended to be used post-operatively and reduces necessary blood transfer to the patient.

In an embodiment of the invention according to FIG. 1
FIG. 1 is a longitudinal cross-sectional view of a hemostasis promoting medical device.

Figure 4C:
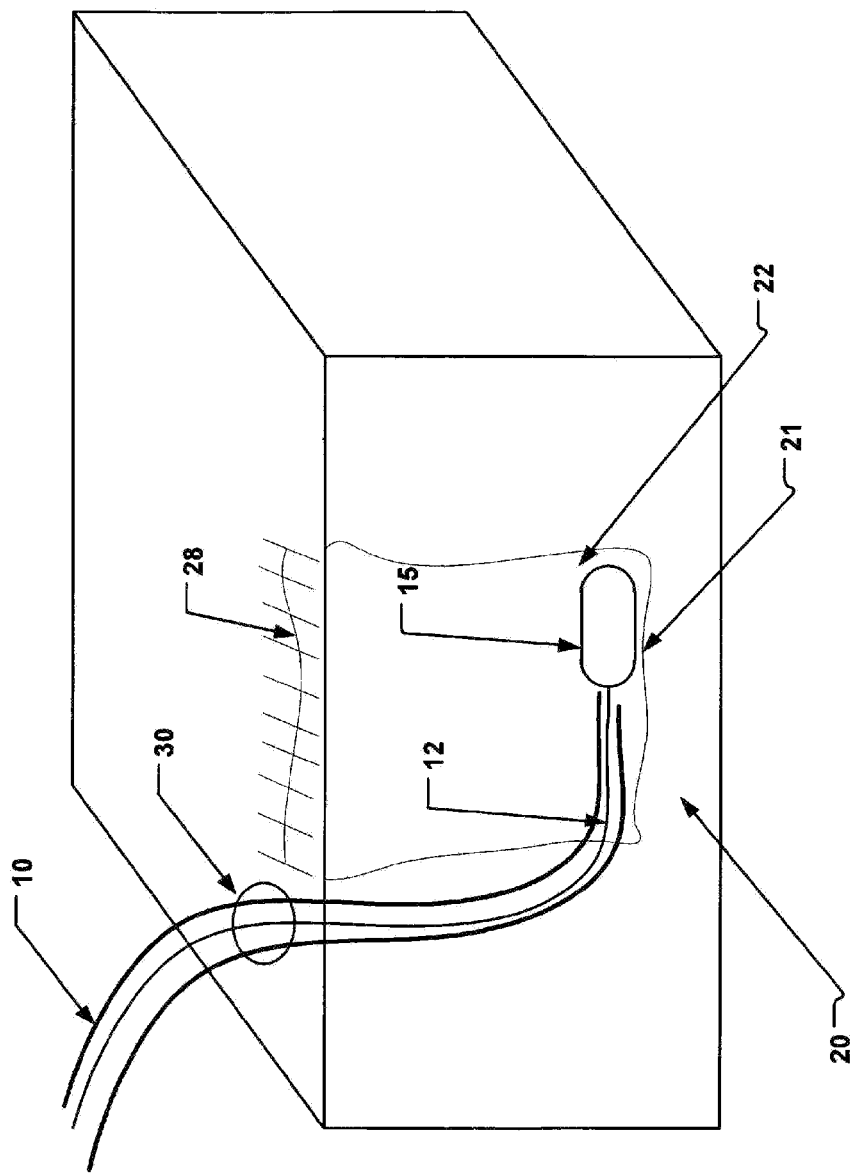
Figure 4D:
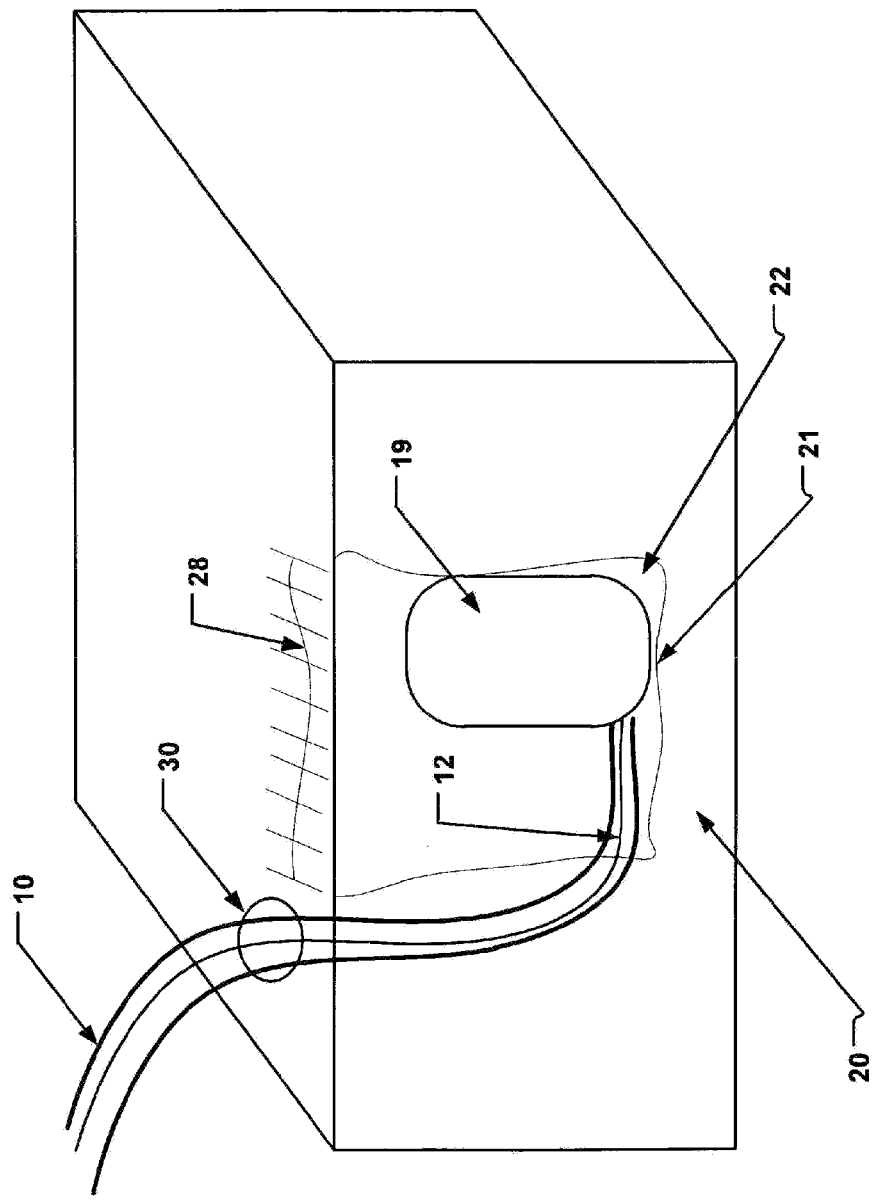
Figure 4E:
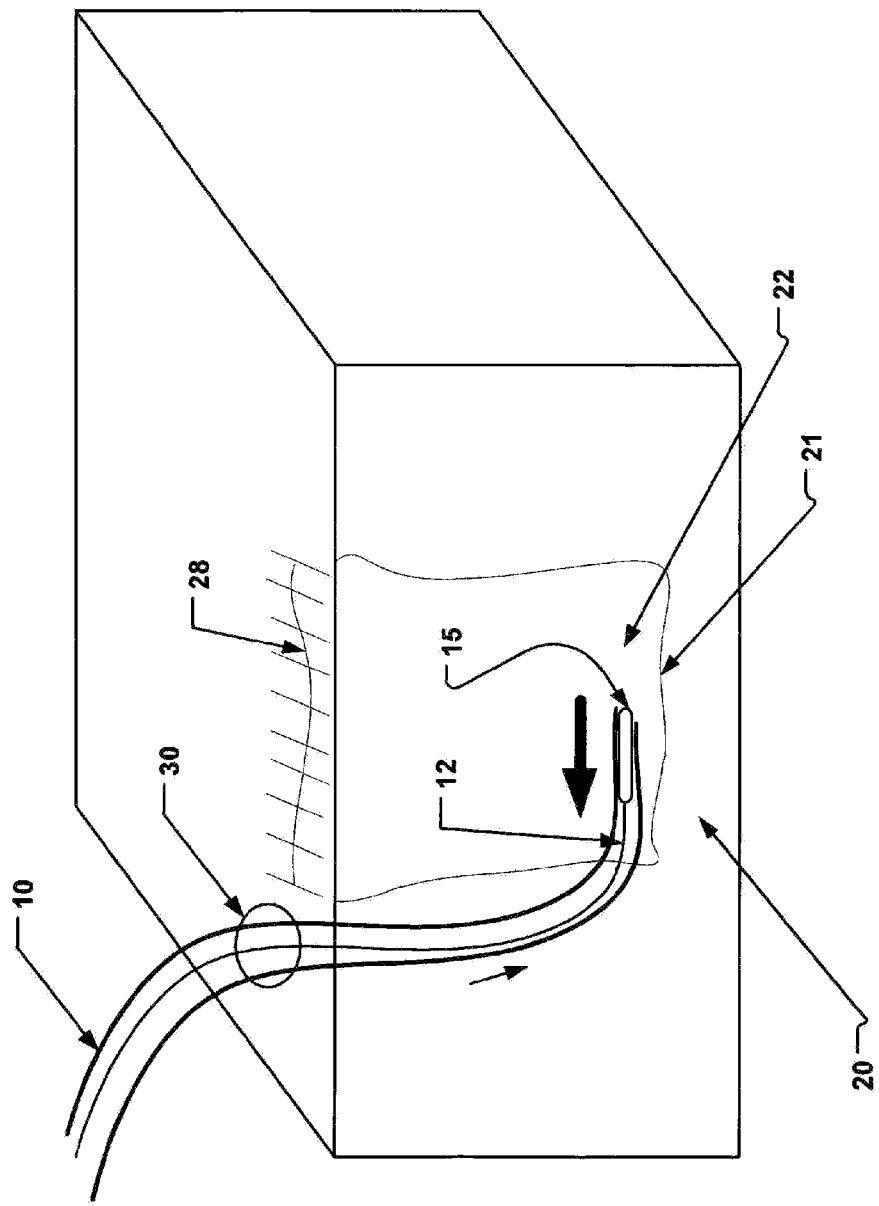
Figure 4F:
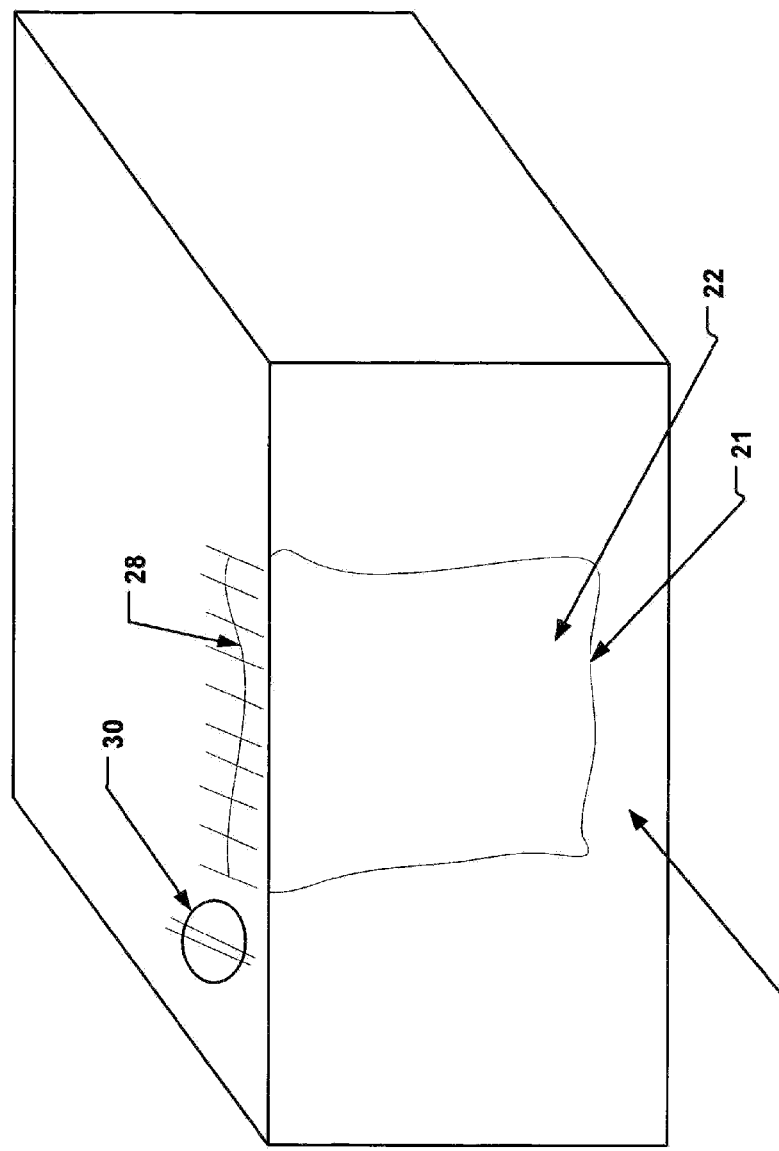
Figure 5:
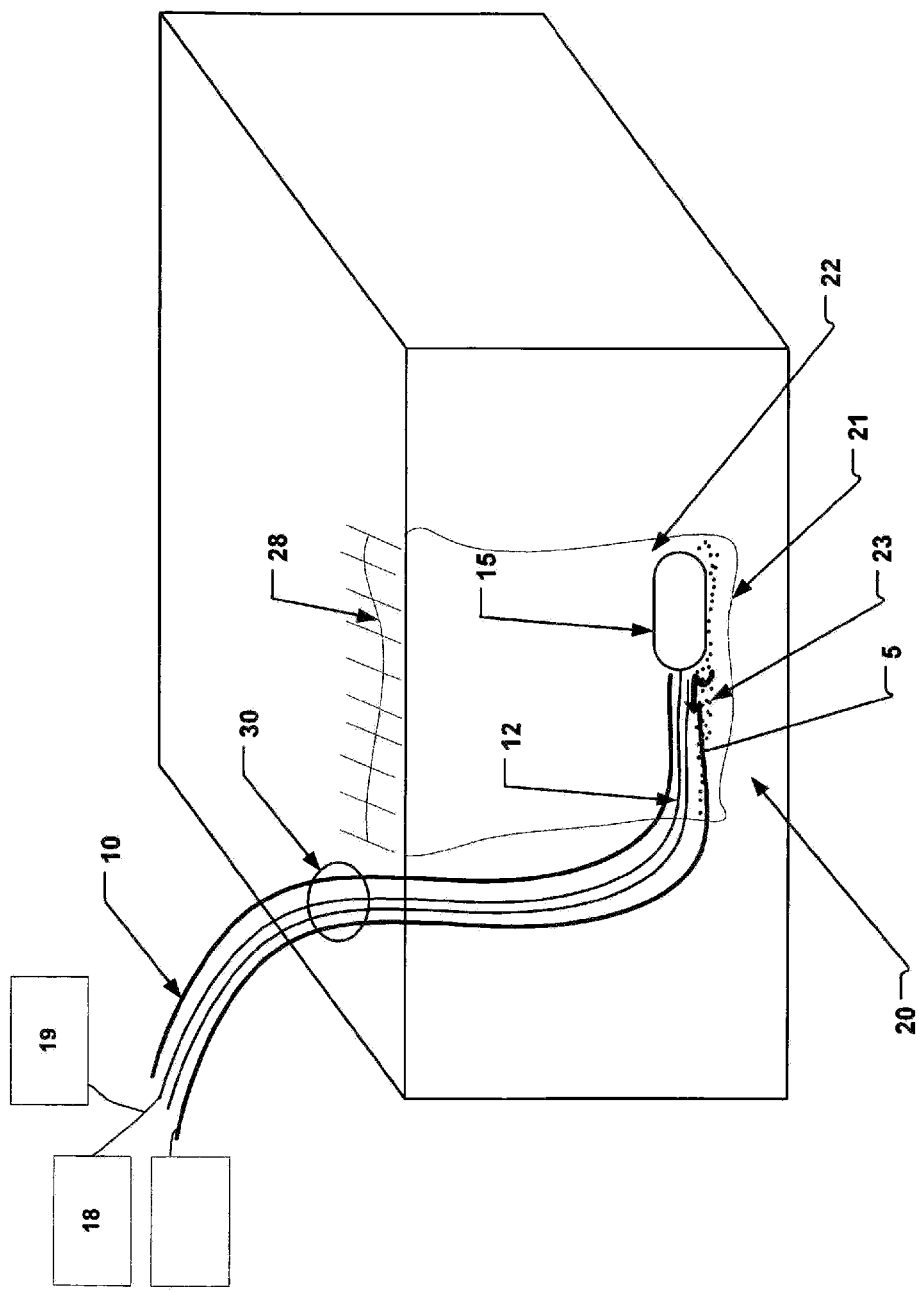
FIG. 5 is schematic views of a confined wound site where a combined hemostasis promoting and wound drainage medical device is applied.
Figure 6:
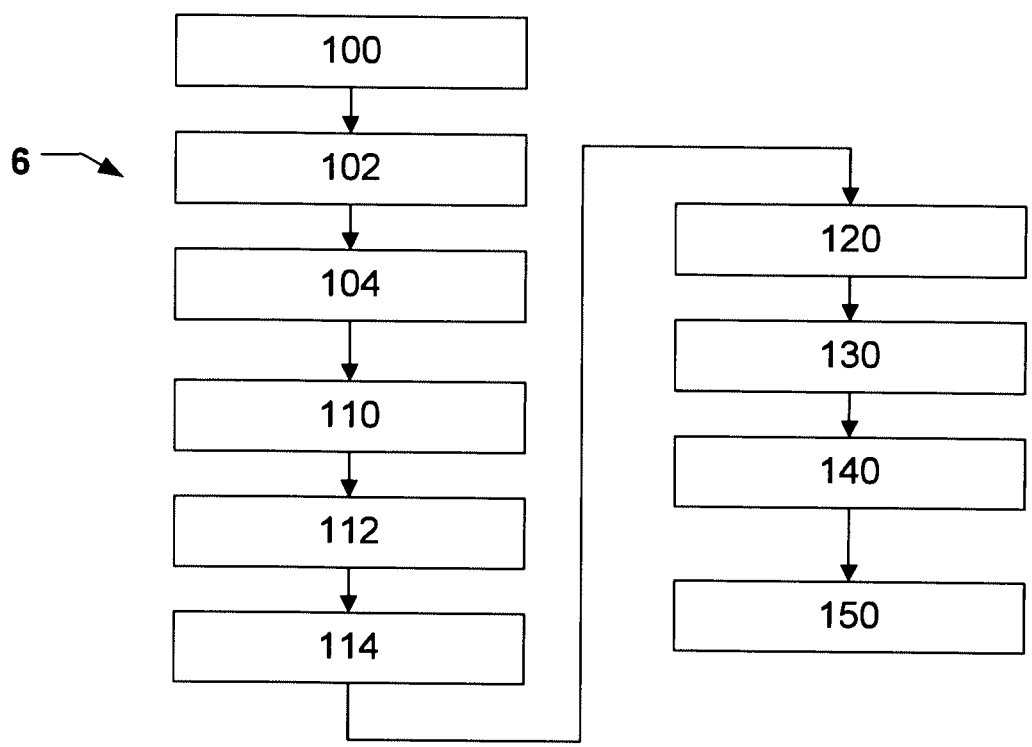
FIG. 6 is a flowchart illustrating a medical procedure of draining exudate from a wound cavity of a post surgical confined wound and promoting hemostasis for therapeutic treatment of the wound.

In FIG. 1 a hemostasis promoting medical device 1 is shown. The device promotes hemostasis in subcutaneous tissue 21 surrounding a wound cavity 22 of a post surgical wound, as shown in FIGS. 4 and 5, which illustrate a medical procedure 6 as shown in FIG. 6.

The device 1 is distally arranged in the tissue 21. As can be seen, e.g. in FIG. 4A, the wound is a confined wound 20 that is cutaneously closed, as illustrated at region 28. The confined wound is for instance closed by suturing or stapling as known in the surgical art.

The device 1 has an elongate sheath 10, which has a proximal end 16 in use arranged outside the wound cavity 22 and a distal end 18 percutaneously delivered into and arranged in the wound cavity 22, see e.g. FIG. 4B. The device 1 is percutaneously installed via a cutaneous opening 30. Alternatively, the sheath 10 may be arranged in an incision at the region 28 before completely closing the incision and confining the wound 20.

The device 1 further has a hollow inflation and deflation tubular member 12 arranged along the elongate sheath 10. An inflatable and deflatable balloon 15 is arranged in fluid communication with the tubular member 12 for controlling a pressure and inflation state of the balloon 15. For insertion into the wound cavity 22, the balloon 15 is arranged in the sheath 10. The balloon 15 may be pre-loaded into the sheath 10. Alternatively, the balloon may be introduced into the sheath 10 upon insertion into the wound cavity 22. The deflated balloon is thus, for instance arranged at the distal end 18, provided longitudinally moveable relative the sheath 10.

The balloon 15 is in a deflated state and arranged proximal to the distal end 18 inside the sheath 10 for delivery to the wound cavity 22 prior to being temporary inflated in the wound cavity 22 (FIG. 4B). The balloon 15 is then inflated and in a temporary inflated state and arranged outside the sheath 10, at least partly in contact with the tissue 21 for the hemostasis promotion (FIG. 4D). Thereafter, the balloon is deflated, e.g. by a vacuum from a pump device (not shown) connected to the proximal end 16 of the tube 12. Thus, the balloon 15 is again in a deflated state and retracted into the sheath 10 for removal from the wound cavity 22 (FIG. 4E). To this end, the deflated balloon 15 is either retracted into the sheath 10, or the sheath 10 is pushed over the deflated balloon 15. Then, the device 1 is retracted from the wound cavity 22 through the opening 30, which then is closed (FIG. 4F). Alternatively, only the balloon may be drawn out of the proximal end of the sheath 10. In this manner, the sheath 10 may be used for further access to the wound cavity 22. For instance, a wound drainage may be provided by a separate lumen of the sheath 10 (see FIGS. 3B, 3C). Alternatively, or in addition, the drainage may be provided through the lumen of the sheath itself. The latter drainage function may also be provided by the sheath when the balloon is positioned beyond the distal end 18 in the wound cavity 22.

In this manner the hemostasis promoting medical device 1 is percutaneously retractable from the confined wound 20.

The balloon 15 and/or the sheath 10 may have an outer surface that is at least partly non-absorbent for liquid and/or non-adhesive to the tissue 21. In addition, the surface is in particular embodiments hydrophobic. Thus clotted blood in the wound cavity 21 does not stick to the balloon 15 and/or sheath 10. The non adherence of the balloon and/or the sheath to the surrounding tissue is provided by the hydrophobic surface thereof. This is in particular advantageous for the long-term use of the medical device. Blood clotting does not occur at such devices to a rate that would make the balloon stick to the vessel. Hence, devices of the embodiments of the invention provide a balance of clot formation in the wound tissue and surrounding vasculature as opposed to formation on the balloon.

The balloon 15 may have a foamy shaped outside structure. The foamy shape may be made by a structure that has as a cell structure. The membrane of the balloon 15 may be made of foam rubber. Thus the membrane of the balloon is elastically compressible. The external outside surface of the foamy shaped structure may be smooth or even without a cell structure, e.g. to prevent ingrowth of endothelial tissue.

The envelope of the inflatable balloon may be expandable, allowing for a resiliently supported deflation and a more compact deflated structure than balloons made of non-expandable membranes.

The balloon 15 has a membrane that is fluid impermeable. In addition, or alternatively, the membrane is non-swelling.

The balloon 15 has a surface that may be provided with an adhesion inhibitor. Alternatively, or in addition, the balloon surface has a pharmaceutical substance arranged at it. The pharmaceutical substance may be arranged as a coating on the membrane of the balloon. Alternatively, the pharmaceutical substance may be arranged in and integrated with the membrane material. The pharmaceutical substance may e.g. be one or more of antibiotics, coagulation promoting agents, platelet adherence reducers, etc.

In an embodiment, the membrane of the balloon 15 is permeable for nitric oxide (NO). When inflated and filled with a liquid releasing the NO, a convenient delivery system for NO to wound cavities is provided. NO generating systems are often toxic. In the embodiments, however, the source of NO is kept separate from the wound tissue, which is advantageous in when the NO generating system is toxic.

The membrane of the balloon 15 is in some embodiments made of polytetrafluoroethylene (PTFE) or hydrophobic microporous polytetrafluoroethylene (PTFE).

The sheath 10 may be flexible such that the device is positionable in the wound 20 before or after it is closed.

In some embodiments, the balloon 15 has arranged therein a bistable support stent 17 that has a first collapsed configuration when the balloon is deflated and a second expanded configuration when the balloon is inflated for supporting a patency of the balloon in the wound cavity.

The device 1 has in certain embodiments a pressure sensor 18, see an illustration in the example of FIG. 5, for regulating an inner pressure of the balloon when inflated. The pressure transducer for the intra balloon pressure is used to provide a desired inflation of the balloon. The size of the balloon is thus controllable. In this manner a desired pressure is applied to the tissue 21 surrounding the wound cavity 22, where the balloon is in apposition with the tissue 21.

The pressure sensor 18 may be used to provide a pressure signal comprising information or measurement data for detection of a dislocation of the balloon when inflated. In this manner e.g. an alarm may be activated. The dislocation may be detected by a control unit of the device (not shown) when a threshold pressure is crossed. The threshold may be crossed towards lower or higher pressures, thus indicating certain types of dislocation.

The device 1 has in certain embodiments an ultrasonic sound generator 19, see FIG. 5, that provides and ultrasonic therapeutic healing of the wound. For instance, when the balloon is inflated with a liquid, and the ultrasonic sound generator 19 is coupled to the liquid at the proximal end of the tube 12, ultrasonic sound waves propagate through the liquid and to the balloon 15 to the tissue 21 for the ultrasonic therapeutic healing.

Figure 2:
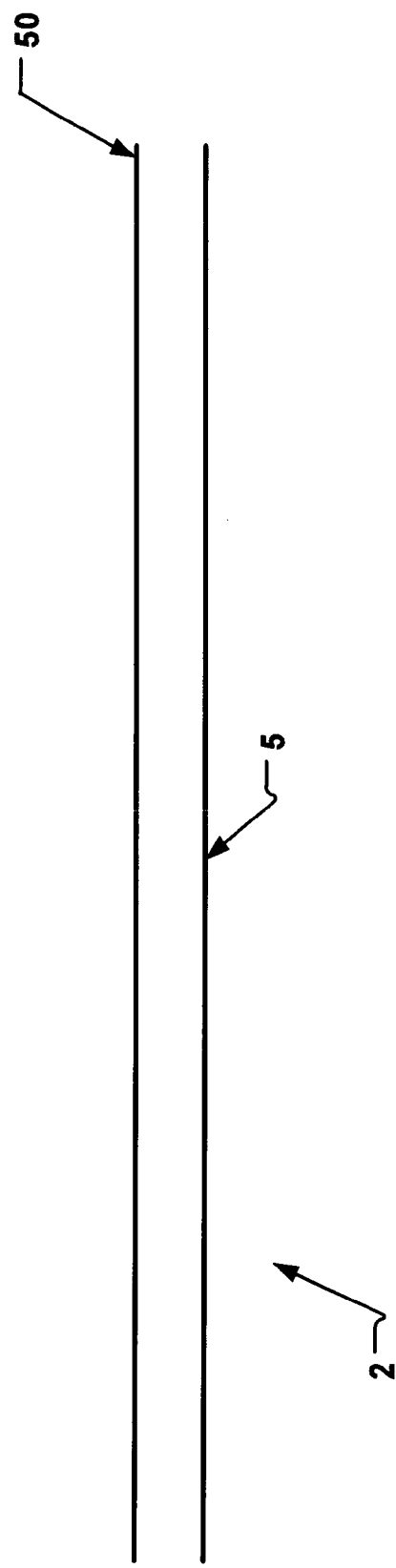
FIG. 2 is a similar cross-sectional view of a medical drainage device.

FIG. 2 shows a drainage device 2 having a fluid communication channel 5. FIG. 5 is schematic views of a confined wound site where a combined hemostasis promoting and wound drainage medical device is applied.

In some embodiments, a combination of a hemostasis promoting medical device 1 and a medical drainage device 2 is provided. The fluid communication channel 5 provides for fluid communication from the wound site, e.g. for removing wound exudate 23 from the wound. The channel 5 has a distal end 50 that in use is arranged in the wound cavity 22.

Figure 3:
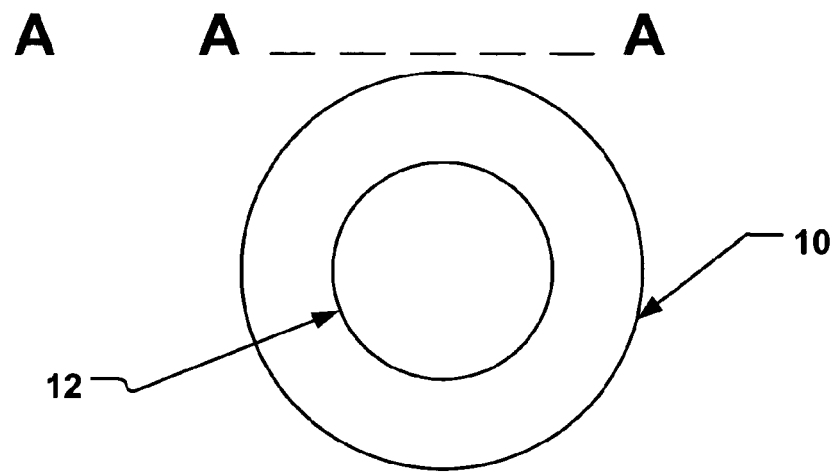
FIG. 3 shows axial cross sections (A) of a hemostasis promoting medical device, and (B and C) of a combined hemostasis promoting and wound drainage medical device.
Figure 3:
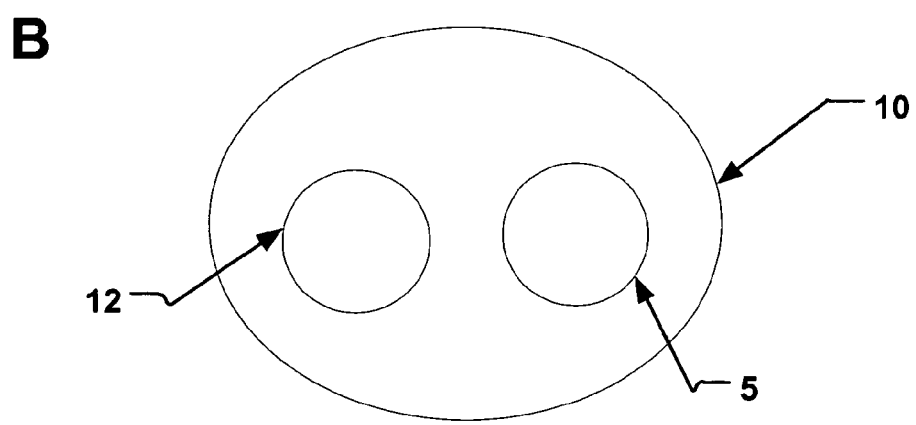
Figure 3:
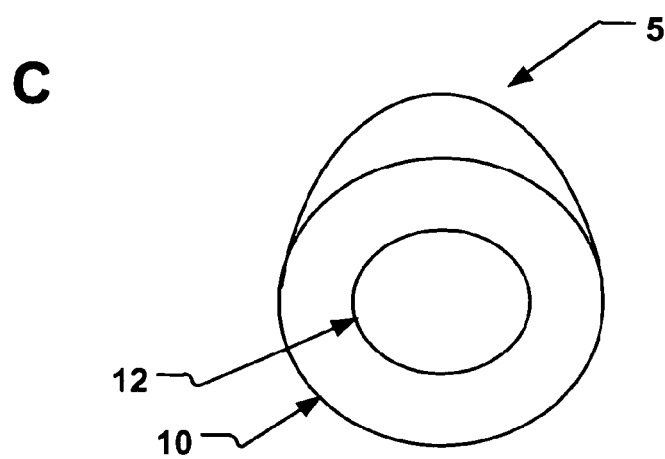

As shown in FIGS. 3B and 3C, such a combined hemostasis promoting and wound drainage medical device is provided in some embodiments as an integrated device. The fluid communication channel 5 is for instance integrally formed with the sheath 10. A medical drainage device is thus provided having at least temporary hemostasis promoting properties.

Medical procedures are now described with reference to FIGS. 4A to 4F and FIGS. 5 and 6. The medical procedure 6 provides draining of wound exudate from a wound cavity of a post surgical confined wound and at the same time promoting of hemostasis for therapeutic treatment of the wound. The procedure includes providing 100 a medical drainage device having a fluid communication channel, and percutaneously arranging 102 a distal end of the fluid communication channel in the wound cavity of the post surgical confined wound and a proximal end of the fluid communication channel outside of the wound cavity. Thus wound exudate is drained 104 from the distal end to the proximal end of the fluid communication channel.

Further, a hemostasis promoting medical device is provided 110 having an elongate sheath, an inflatable and deflatable balloon longitudinally moveable relative the sheath, and a hollow inflation and deflation tubular member along the elongate sheath in fluid communication with the balloon. The procedure comprises percutaneously arranging 112 a proximal end of the elongate sheath outside the wound cavity and a distal end of the elongate sheath in the wound cavity with the balloon deflated in the sheath, and discharging 114 the balloon out of the distal end of the sheath in the wound cavity thereof.

The procedure continues with inflating 120 the balloon to a desired pressure through the tubular member to be at least partly in apposition with tissue surrounding the wound cavity for the hemostasis promotion during a hemostasis promoting time.

Then the balloon is deflated 130, and the deflated balloon is reloaded 140 into the distal end of the sheath. Finally, the distal end of the sheath is retracted 150 out of the wound cavity.

The deflated balloon is reloaded into the sheath by moving the sheath longitudinally relative the balloon. This is for instance done including retracting the hollow tubular member and thus the balloon into the sheath, or pushing the sheath over the deflated balloon.

The hemostasis promoting time is between six and up to twenty-four hours, preferably between eight to twelve hours before deflating the balloon and withdrawing the balloon and/or sheath.

The procedure is a non-acute, planned procedure initiated during termination of a surgical intervention.

The procedure is for instance a thorax surgical intervention and the draining provides preventing of a tamponage by the wound cavity.

A gas pressure lower than a gas pressure in the wound cavity is in some embodiments applied to the distal end of the fluid communication channel in the wound cavity for promoting the drainage function.

The inflated balloon provides a positive mechanical pressure at the apposition for the hemostasis promotion. The balloon is for instance flexible to make contact with the tissue substantially independent of a topography of the tissue surrounding the wound cavity.

The procedure provides for the confined wound not needing to be opened again during a healing phase.

The present invention has been described above with reference to specific embodiments. However, other embodiments than the above described are equally possible within the scope of the invention. The scope of the invention is only limited by the appended patent claims.

The invention claimed is:

1. A medical procedure of draining exudate from a wound cavity of a post surgical confined wound and promoting hemostasis for therapeutic treatment of said wound, said procedure comprising:
   surgically creating a cutaneous opening at a distance from said confined wound;
   providing a medical drainage device having a fluid communication channel;
   percutaneously arranging a distal end of said fluid communication channel in said wound cavity of said post surgical confined wound and a proximal end of said fluid communication channel outside of said wound cavity, and thus draining wound exudate from said distal end to said proximal end of said fluid communication channel;
   cutaneously closing said confined wound;
   providing a hemostasis promoting medical device having an elongate sheath, an inflatable and deflatable balloon longitudinally moveable relative to said sheath, and a hollow inflation and deflation tubular member along said elongate sheath in fluid communication with said balloon;
   percutaneously arranging said sheath through said cutaneous opening with a proximal end of said elongate sheath outside said wound cavity and a distal end of said elongate sheath in said wound cavity with said balloon deflated in said sheath;
   discharging said balloon out of said distal end of said sheath in said wound cavity thereof;
   inflating said balloon to a desired pressure through said tubular member to be at least partly in apposition with tissue surrounding said wound cavity for said hemostasis promotion during a hemostasis promoting time; and
   deflating said balloon, reloading said deflated balloon into said distal end of said sheath, and retracting said distal end of said sheath out of said wound cavity through said cutaneous opening;
   wherein the procedure further comprises providing nitric oxide (NO) to tissue of said wound emanating from a liquid being a source of nitric oxide (NO) inside said balloon, said balloon being filled with said liquid when inflated and being fluid impermeable whereby the liquid source of nitric oxide (NO) is kept separate from the wound tissue, and said balloon being permeable for nitric oxide (NO); and,
   providing an ultrasonic sound generator, generating ultrasonic sound waves with said ultrasonic sound generator, and propagating said ultrasonic sound waves through said liquid towards said inflated balloon and through said balloon to said surrounding tissue.

2. The procedure of claim 1, wherein said deflated balloon is reloaded into said sheath by moving said sheath longitudinally relative to said balloon, including retracting said hollow tubular member and thus said balloon into said sheath, or pushing said sheath over said deflated balloon.

3. The procedure of claim 1, wherein said hemostasis promoting time is between six and twenty-four hours before deflating said balloon and withdrawing said medical drainage device.

4. The procedure of claim 1, wherein said procedure is a non-acute, planned procedure initiated during termination of a surgical intervention.

5. The procedure of claim 1, wherein said surgical intervention is a thorax surgical intervention and said procedure comprises preventing a tamponage by draining said wound cavity.

6. The procedure of claim 1, comprising applying a gas pressure to said distal end of said fluid communication channel wherein said gas pressure is lower than a gas pressure in said wound cavity.

7. The procedure of claim 6, comprising providing by said inflated balloon a positive mechanical pressure at said apposition with tissue surrounding said wound cavity providing said hemostasis promotion, and wherein said balloon is flexible making contact with said tissue substantially independent of a topography of said tissue surrounding said wound cavity.

8. The procedure of claim 1 or 6, comprising providing by said inflated balloon a positive mechanical pressure at said apposition with tissue surrounding said wound cavity providing for said hemostasis promotion, and wherein said balloon is flexible making contact with said tissue substantially independent of a topography of said tissue surrounding said wound cavity.

9. The procedure of claim 1, wherein the confined wound is not opened again during healing.

10. The procedure of claim 1, comprising retracting said balloon after stopping of bleeding, and keeping the drainage device in place for continued wound exudate handling.

11. The procedure of claim 1, comprising promoting coagulation by said hemostasis promoting medical device for controlling a bleeding situation.

12. The procedure of claim 1, comprising removing said balloon and/or sheath from the wound without causing bleeding.

13. The procedure of claim 1, comprising providing at least one pharmaceutical substance from said hemostasis promoting medical device to said wound.

14. The procedure of claim 13, wherein said pharmaceutical substance includes at least one of an antibiotic agent, a coagulation promoting agent, or a platelet adherence inhibitor.

15. The procedure of claim 1,
   wherein said balloon has an outer surface that is hydrophobic.

16. A medical procedure of draining exudate from a wound cavity of a post surgical confined wound and promoting hemostasis for therapeutic treatment of said wound, said procedure comprising:
   surgically creating a cutaneous opening at a distance from said confined wound;
   providing a medical drainage device having a fluid communication channel;
   percutaneously arranging a distal end of said fluid communication channel in said wound cavity of said post surgical confined wound and a proximal end of said fluid communication channel outside of said wound cavity, and thus draining wound exudate from said distal end to said proximal end of said fluid communication channel;

cutaneously closing said confined wound;

providing a hemostasis promoting medical device having an elongate sheath, an inflatable and deflatable balloon longitudinally moveable relative to said sheath, and a hollow inflation and deflation tubular member along said elongate sheath in fluid communication with said balloon;

percutaneously arranging said sheath through said cutaneous opening with a proximal end of said elongate sheath outside said wound cavity and a distal end of said elongate sheath in said wound cavity with said balloon deflated in said sheath;

discharging said balloon out of said distal end of said sheath in said wound cavity thereof;

inflating said balloon with a liquid to a desired pressure through said tubular member to be at least partly in apposition with tissue surrounding said wound cavity for said hemostasis promotion during a hemostasis promoting time;

providing an ultrasonic sound generator, generating ultrasonic sound waves with said ultrasonic sound generator, and propagating said ultrasonic sound waves through said liquid towards said inflated balloon and through said balloon to said surrounding tissue.

17. The procedure of claim 16, wherein the procedure further comprises providing nitric oxide (NO) to tissue of said wound emanating from said liquid being a source of nitric oxide (NO) inside said balloon, said balloon being filled with said liquid when inflated and being fluid impermeable whereby the liquid source of nitric oxide (NO) is kept separate from the wound tissue, and said balloon being permeable for nitric oxide (NO).

* * * * *